United States Patent [19]

Redeaux, Jr.

[11] 4,427,015

[45] Jan. 24, 1984

[54] SYRINGE FOR USE IN THE WITHDRAWAL OF ARTERIAL BLOOD

[76] Inventor: Ralph Redeaux, Jr., 3516 Greinwich Blvd., Lake Charles, La. 70605

[21] Appl. No.: 311,938

[22] Filed: Oct. 16, 1981

Related U.S. Application Data

[63] Continuation-in-part of Ser. No. 157,193, Jun. 6, 1980, abandoned.

[51] Int. Cl.$^3$ ............................................. A61B 5/14
[52] U.S. Cl. ...................................... 128/765; 604/187
[58] Field of Search .............. 128/760, 763, 765–766, 128/274, 278, 215–216, 218 R, 218 P, 218 PA, 219–220, 234–235, 237; 73/864.62–864.64, 863.71–863.73; 604/51–52, 118, 131, 187, 184, 239, 319–320

[56] References Cited

U.S. PATENT DOCUMENTS

| | | | |
|---|---|---|---|
| 3,577,980 | 5/1971 | Cohen | 128/278 X |
| 3,648,684 | 3/1972 | Barnwell et al. | 128/764 |
| 3,960,139 | 6/1976 | Bailey | 128/765 X |
| 3,965,897 | 6/1976 | Lundquist | 128/237 X |
| 4,008,718 | 2/1977 | Pitesky | 128/218 R |
| 4,073,288 | 2/1978 | Chapman | 128/765 |
| 4,091,677 | 5/1978 | Oshikubo | 128/218 P X |
| 4,326,541 | 4/1982 | Eckels | 128/274 X |

Primary Examiner—Lee S. Cohen
Assistant Examiner—Angela D. Sykes
Attorney, Agent, or Firm—Llewellyn A. Proctor

[57] ABSTRACT

A syringe for the collection of arterial blood, that offers near zero resistance to blood flow, eliminates arterial-venous admixing due to aspiration, prevents air trapping, and does not require a lubricant. The syringe embodies a tubular body, a plunger with valve and capillary bore for its entire length. The forward end of plunger is concaved to center at 45 degrees. The capillary bore is communicated with the chamber through said concave surface. The plunger is valved to provide for the withdrawal, and trapping of arterial blood in the chamber. The capillary bore and valve assist operation with self-aspirating analyzers. By nature of friction between the plunger and chamber wall, the device is volume selective.

1 Claim, 2 Drawing Figures

SYRINGE FOR USE IN THE WITHDRAWAL OF ARTERIAL BLOOD

RELATED APPLICATION

This is continuation-in-part of application Ser. No. 157,193, filed June 6, 1980, now abandoned.

Over the years catheters and syringes have been developed for medical use, particular reference being made to the latter. Syringes are employed for the injection of drugs into the body, and for the withdrawal or drawing of blood from the body. Syringes are typically used for the withdrawal of arterial blood specimens needed for blood gas analysis.

Unfortunately, present syringes suffer certain deficiencies. Some offer too much resistance to blood flow which, in turn, makes the more routine collection of blood from patients with low blood pressure quite difficult, this often necessitating femoral and brachial punctures. Air is often trapped in the blood specimen. Mixed samples of venous and arterial blood are inadvertently taken for testing rather than undiluted arterial blood due to aspiration. The plungers of present syringes are often sluggish, or slippery and difficult to operate. It is often necessary to use heparin as a lubricant.

It is, accordingly, the primary object of the present invention to obviate these and other disadvantages associated with prior art syringes.

A particular object is to provide a novel syringe useful for taking arterial blood from patients, especially a syringe which allows the taking of arterial blood with minimal resistance to blood flow, or the trapping of air.

A further object is to provide a syringe as characterized which can be used to collect arterial blood with minimal admixing of venous blood, if any, especially one which does not require the use of a lubricant such as heparin to facilitate its operation.

Yet another object is to provide a syringe useful, and operable with self aspirating analyzers. These objects and others are achieved in accordance with the present invention which embodies a syringe constituted of a tubular body, a cannula or tubular needle disposed on the distal or forward end thereof, and a large diameter hollow plunger reciprocally mounted within the proximate or rearward end of said tubular body. The tubular body is provided with an expandable chamber, the chamber being expandable by retraction of the plunger. The forward face of the plunger is concave, or recessed inwardly, a lumen or bore of capillary size, which extends the length of the plunger, being communicated with the recess, or chamber, formed by the concave, or recessed surface. Preferably, the concave face of the plunger is formed by the provision of a frusto-conic opening of total included angle ranging from about 45 to about 135 degrees, the apex of the frusto-conic opening forming the point of entry to the communicating bore which extends through the plunger. By virtue of this feature minimal amounts of oxygen, if any, are trapped within the chamber, or at the face of the plunger. The rearward segment of the plunger through which the bore is extended is valved such that the communication which extends, generally axially, from the dispensing end of the needle, expandable chamber, and plunger can be alternately opened and closed as required in the operation of the syringe. The valve and capillary bore makes possible operations with self aspirating analyzers.

The invention, and its purpose of operation, will be more fully understood by reference to the following detailed description of a specific, and preferred embodiment, and to the attached drawings to which reference is made in the description. In the drawing, similar numbers are used to represent similar parts or components. Subscripts are used to represent subcomponents.

Figure 1:
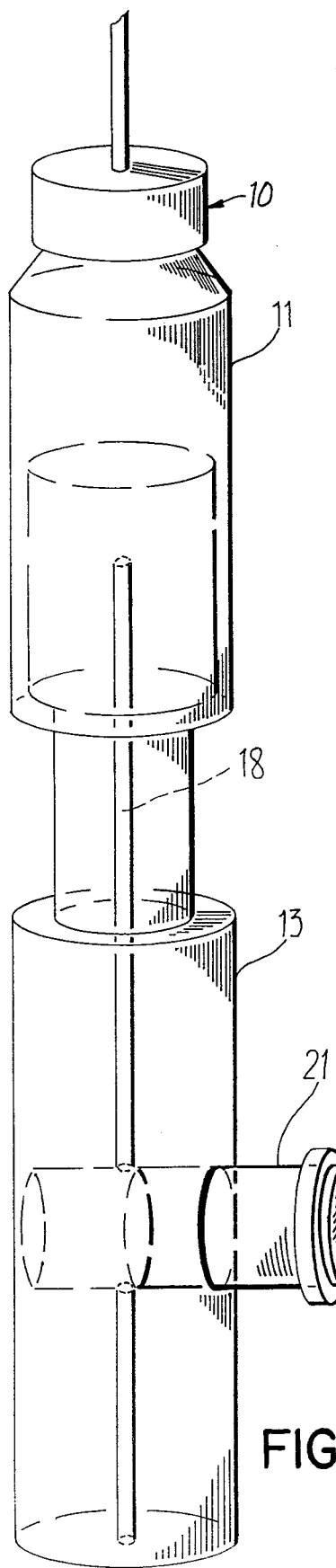
FIG. 1 is a perspective, side elevation view of a preferred syringe.
Figure 2:
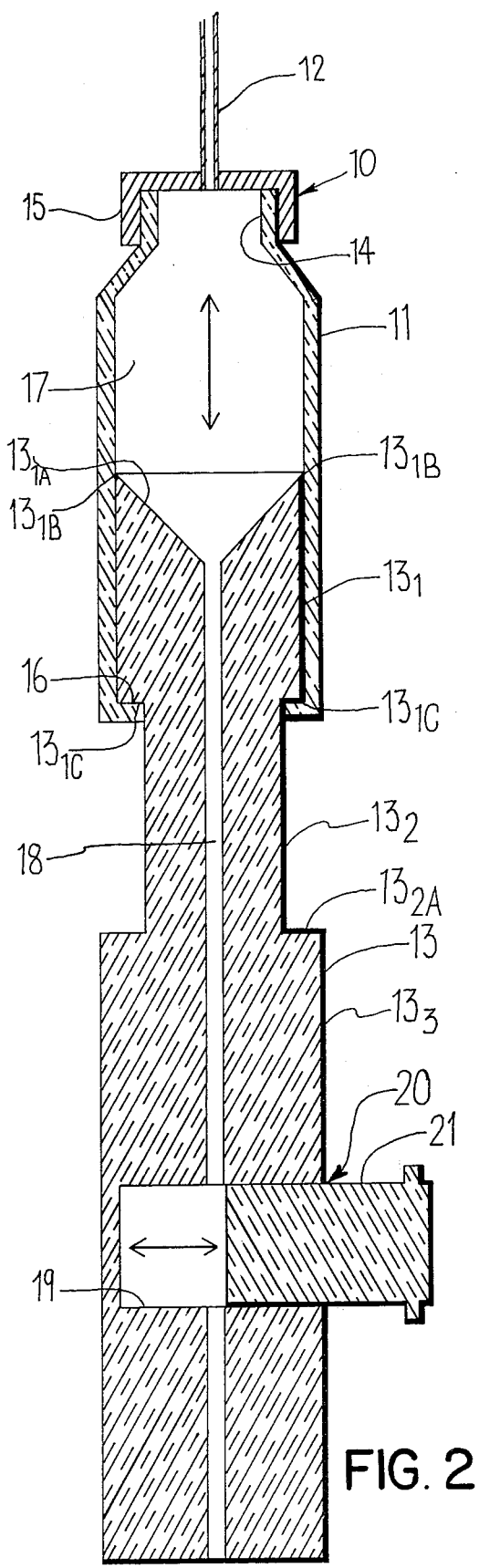
FIG. 2 is a sectional view of the syringe depicted by reference to the preceding figure.

Referring to the figures, notably FIG. 1, there is shown a preferred syringe 10 constituted generally of a tubular body 11, at the forward end of which is fitted a tubular needle 12. Within the rearward end of the tubular body 11 there is slidably mounted, or fitted, a reciprocable hollow plunger 13. The forward end of the tubular body 11 is constituted of a projecting segment 14 of reduced diameter which forms a base, or site upon which the tubular needle 12 can be mounted as via an open centered cap or via a hub 15, the underside of which can be mated with said base, and the inner surface of which, can be seated, epoxied or otherwise secured and sealed upon the projection 14. The rearward end of the tubular body 11 is provided with a inwardly projecting flange 16 designed to hold the slidably mounted hollow plunger 13 in place within said tubular body 11.

The forward face of the plunger 13 is recessed, or provided with a frusto-conic shaped entry $13_{1A}$ at the center of which is located the forward entry to a lumen or bore 18 of capillary size which extends the length of the plunger 13.

The external diameter of the forward end $13_1$ of the reciprocable hollow plunger 13 is substantially equal to the internal diameter of cylindrical shaped chamber 17 formed by the enclosing wall of the tubular body 11. The rearward portion $13_3$ of the reciprocable hollow plunger 13 is of external diameter substantially equal or larger than the external diameter of the forward end $13_1$ of the plunger, and the intermediate portion $13_2$ of the plunger 13 is of smaller diameter than the forward or rearward ends $13_1$, $13_3$ of the plunger 13. The forward end $13_1$ of the plunger 13 is fitted within, and slidably movable the length of the chamber 17. In its extreme forward position the terminal forward end $13_{1B}$ flushes with the wall at the forward end of the chamber 17, and the forward face of the projecting edge $13_{2A}$ of the enlarged position $13_3$ of the plunger flushes with the rearward face of the flange 16. In its extreme rearward position the rearward projecting edge $13_{1C}$ of the forward end $13_1$ of the plunger abutts the forward face of the flange 16. In the extreme forward position of the plunger 13 the chamber 17 is of limited volumetric capacity, or capacity equal to that defined by the frusto-conic entry provided in the face of the plunger. In its extreme rearward position the chamber 17 is of maximum volumetric capacity.

The rearward portion $13_3$ of the plunger 13 is valved, or provided with a valve 20 constituted of a laterally oriented cylindrical shaped opening 19 which intersects the lumen or bore 18, and within which a slidable stem 21 is snugly mounted. Movement of the stem 21 inwardly within the opening 19 to block the luman or bore 18 effects closure of the valve 20. Retraction, or withdrawal of the stem 21 from the opening 19 unblocks the lumen or bore 18 and, in effect, opens the valve 20.

In operation, the plunger 13 is retracted to open the chamber 17 to the desired volumetric capacity. Thereafter, until completion of the blood sampling operation the plunger remains stationary. The valve 20 is opened by retraction, or withdrawal of stem 21 from the lateral opening 19 to unblock the lumen or bore 18. The tip of the cannula, or needle 12, is then projected into an artery from which an arterial blood specimen is to be removed. This done, blood is pumped via action of the patient's heart through the hollow needle 12 into the chamber 17 of the syringe 10. On filling the chamber 17 with blood, blood then enters the lumen or capillary bore 18 and flows therethrough. The valve 20 is closed, to trap the specimen, by inward projection of the stem 21 into the lateral opening 19. The needle 12 is then withdrawn from the artery of the patient and the arterial blood specimen then taken from the chamber of the syringe 10 by forward movement of the plunger 13 to project the blood from the dispensing end of the needle 12 to a specimen collection source for analysis. For self-aspirating analyzers, the valve may be opened if necessary to allow vacuum through syringe to aid operation.

It is apparent that various substitutions, modifications and changes, such as in the location, or in the relative and absolute dimensions of the parts, size, shape, materials used and the like, can be made without departing the spirit and scope of the invention as will be apparent to those skilled in the art.

Having described the invention, what is claimed is:

1. In apparatus useful for the collection of arterial blood which embodies a tubular body, inclusive of a chamber of relatively large diameter formed therein by an enclosing wall, said tubular body having a forward end and a rearward end, a tubular needle having a dispensing end affixed on the forward end of said tubular body, said needle having an opening therethrough being in communication with said chamber, a plunger having a forward portion and a rearward portion reciprocably fitted within the chamber of said tubular body, the external diameter of the forward portion of which is substantially equal to the internal diameter of the chamber within which the forward portion of said plunger is fitted, the improvement comprising a frusto-conic shaped entry, the included angle formed by the frusto-conic entry ranging from about 45° to about 135°, located in the forward portion of the plunger to provide a permanent opening into the chamber regardless of the position of the plunger, a capillary bore extending from the apex of said frusto-conic shaped entry in the forward portion of said plunger throughout the length of the plunger, and a fast acting valve located within the rearward portion of the plunger, said valve being formed by a lateral opening extending from an outer surface of the plunger to intersect the capillary bore, and a stem slidably movable within said lateral opening for rapidly closing the valve by closure of said capillary bore and thereby creating an obstruction in the bore, or movable within said opening for opening the valve by removing from the bore the obstruction created by the stem, whereby, with the valve open and the plunger positioned to adjust the size of the chamber, the dispensing end of the tubular needle is adapted to be inserted within an artery and arterial blood collected until such time that the chamber is filled, and the valve then closed to trap the arterial blood within the chamber.

* * * * *